US007723467B2

(12) United States Patent
Lipkowski et al.

(10) Patent No.: US 7,723,467 B2
(45) Date of Patent: May 25, 2010

(54) ANTIMICROBIAL COMPOUNDS

(75) Inventors: Andrzej W. Lipkowski, Warsaw (PL); Daniel B. Carr, Chestnut Hill, MA (US)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 11/180,971

(22) Filed: Jul. 13, 2005

(65) Prior Publication Data

US 2006/0030532 A1 Feb. 9, 2006

Related U.S. Application Data

(62) Division of application No. 09/988,792, filed on Nov. 20, 2001, now abandoned.

(60) Provisional application No. 60/252,369, filed on Nov. 21, 2000.

(51) Int. Cl.
*A61K 38/00* (2006.01)
*A61K 9/00* (2006.01)
*A61K 8/02* (2006.01)
*A01N 25/34* (2006.01)
*A61K 38/04* (2006.01)

(52) U.S. Cl. .................. 530/300; 424/400; 424/401; 424/402; 424/404; 514/2; 530/327

(58) Field of Classification Search ................ 424/1.45, 424/404, 405; 514/15; 530/300
See application file for complete search history.

(56) References Cited

U.S. PATENT DOCUMENTS

| | | | | |
|---|---|---|---|---|
| 4,481,139 | A | * 11/1984 | Folkers et al. | ............ 260/112.5 |
| 5,861,313 | A | 1/1999 | Pang et al. | .................. 435/347 |
| 5,876,948 | A | * 3/1999 | Yankner | .................... 435/7.21 |
| 6,063,758 | A | 5/2000 | Lappi et al. | ..................... 514/2 |
| 6,203,803 | B1 | * 3/2001 | De La Charriere et al. | .. 424/401 |

FOREIGN PATENT DOCUMENTS

| | | | |
|---|---|---|---|
| WO | WO 83/01251 | * | 4/1983 |
| WO | WO 88/07551 | * | 10/1988 |
| WO | WO 92/18536 | * | 10/1992 |
| WO | WO 88/07551 | * | 10/1998 |
| WO | 00/43040 | | 7/2000 |

OTHER PUBLICATIONS

De Simone et al, Journal of Clincal Lab Anal., 1989, 3(6):345-349.*
Maszczynska et al, Analgesia, vol. 3, pp. 259-268, 1998.*
De Simone et al, Journal of Clinical Lab Anal.,1989, 3(6):345-349.*
Schroeder et al, Acta virologica, Sep. 1986, 30(5), p. 432-335.*
Riegler et al, The American Physiological Society, 1999.*
Bowie et al (Science, 1990, 257:1306-1310).*
Greenspan et al. (Nature Biotechnology 17: 936-937, 1999).*
De Simone et al (Journal of Clinical Lab Anal.,1989, 3(6):345-349)(Abstract only).*
Schroeder et al (Acta virologica, Sep. 1986, 30(5), p. 432-335)(Abstract only).*
Sohnle et al (Journal of Infectious Disease, 1991, 163 pp. 187-192).*
Greenspan et al. (Nature Biotechnology 7: 936-937, 1999).*
McGuinnes et al. (Mol. Microbiol. 7:505-514, Feb. 1993).*
Agerberth et al (European Journal of Biochemistry, vol. 202, No. 3, Dec. 1991).*
Payan (Annual Review of Medicine, vol. 40, 1989, pp. 341-352).*
Nicolas et al (Annu. Rev. Microbial. 1995, 49:277-300).*
Niidome et al (Bull. Chem. Soc. Hpn., 73,p. 1397-1402, 2000).*
Agerberth, B. et al., "Amino acid sequence of PR-39 Isolation from pig intestine of a new member of the family of proline-arginine-rich antibacterial peptides", Eur. J. Biochem., vol. 202, No. 3, pp. 849-854 (1991).
Beaucage, S.L. et al., "Deoxynucleoside Phosphoramidities—A new class of key intermediates for deoxypolynucleotide synthesis", Tetrahedron Letters, vol. 22, No. 2, pp. 1859-1862 (1981).
Hartung, H.P. et al., "Substance P: Binding Properties and Studies on Cellular Responses in Guinea Pig Macrophages", The Journal of Immunology, vol. 136, No. 10, pp. 3856-3863 (1986).
Higgins, D.G. et al., "Fast and sensitive multiple sequence alignments on a microcomputer", CABIOS Communications, vol. 5, No. 2, pp. 151-153 (1989).
Jeon, H.K. et at., "Substance P augments nitric oxide production and gene expression in murine macrophages", Immunopharmacology, vol. 41, pp. 219-226 (1999).
Joos, G.F. et al., "Pro-inflammatory effects of substance P: new perspectives for the treatment of airway diseases?", Trends in Pharmacological Sciences, vol. 21, pp. 131-133 (2000).
Linnik, M.D. et al., "Identification of Immunoreactive Substance P in Human and Other Mammalian Endothelial Cells", Peptides, vol. 10, pp: 957-962 (1989).
Maszczynska, I. et al., "Dual Functional Interactions of Substance P and Opioids in Nociceptive Transmission: Review and Reconciliation", Analgesia, vol. 3, pp. 259-268 (1998).
Merrifield, R.B., "Solid Phase Peptide Synthesis. I. The Synthesis of a Tetrapeptide", J. Am. Chem. Soc., vol. 85, pp. 2149-2154 (1963).
Misicka, A. et al., "Topographical Requirements for Delta Opioid Ligands: Presence of a Carboxyl Group in Position 4 is not Critical for Deltorphin High Delta Receptor Affinity and Analgesic Activity", Biochemical & Biophysical Research Communications, vol. 180, No. 3, pp. 1290-1297 (1991).
Payan, D.G., "Neuropeptides and Inflammation:The Role of Substance P", Annual Review of Medicine, vol. 40, pp. 341-352 (1989).
Shibata, H. et al., "Analysis of the mechanism of histamine release induced by substance P", Biochimica et Biophysica Acta, vol. 846, pp. 1-7 (1985).
Yokota, Y. et al., "Molecular Characterization of a Functional cDNA for Rat Substance P Receptor", The Journal of Biological Chemistry, vol. 264, No. 30, pp. 17649-17652 (1999).

(Continued)

*Primary Examiner*—Vanessa L. Ford
(74) *Attorney, Agent, or Firm*—Mintz, Levin, Cohn, Ferris, Glovsky and Popeo, P.C.

(57) ABSTRACT

The invention features an antimicrobial composition comprising a substance P peptide and methods of inhibiting growth of a microorganism by contacting the microorganism with a substance P peptide. Bacterial and fungal pathogens are inhibited by the substance P compositions.

4 Claims, 1 Drawing Sheet

OTHER PUBLICATIONS

Rameshwar, P. et al., "In vitro stimulatory effect of substance P on hematopoiesis", Blood, vol. 81, No. 2, pp. 391-398 (1993).

Folkers, H. et al., "Design and synthesis of effective antagonists of substance P Acta Chemica Scandinavica—Series B", Organic Chemistry & Biochemistry, vol. 36, No. 6, pp. 389-395 (1982).

Selsted, M.E. et al., "Indolicidin, a novel bactericidal tridecapeptide amide from neutrophils", Journal of Biological Chemistry, vol. 267, No. 7, pp. 4292-4295 (1992).

Pascual, D.W. et al., "Substance P production by P388D1 macrophages: a possible autocrine function for this neuropeptide", Immunology, vol. 71, No. 1, pp. 52-56 (1990).

Warren, L.V., "Six Easier Pieces: Discovering the 3D structure of Substance P, using only free internet tools", pp. 1-8 (Jun. 1999); [online] [retrieved on Nov. 14, 2001]. Retrieved from the Internet, URL:http://www.wdv.corn/Notebook/Biochemistry/SubstanceP.

* cited by examiner

Fig. 1

ANTIMICROBIAL COMPOUNDS

RELATED APPLICATION

This application is a divisional of patent application U.S. Ser. No. 09/988,792, filed Nov. 20, 2001 now abandoned, which claims the benefit of provisional application U.S. Ser. No. 60/252,369, filed Nov. 21, 2000, which is hereby incorporated hereby by reference.

GOVERNMENT FUNDING

This invention made with U.S. Government support under DA06284 awarded by the National Institute of Health. The Government has certain rights in the invention.

TECHNICAL FIELD

This invention relates to novel antimicrobial compounds derived from peptides.

BACKGROUND

Widespread use of antibiotics in recent decades has led to proliferation of pathogens having multiple drug resistance, often encoded by transmissible plasmids, and therefore capable of spreading rapidly between species. Many previously useful antibiotics are no longer effective against infectious organisms isolated from human and animal subjects. The specter of epidemic forms of bacterial diseases such as tuberculosis and fungal diseases, which are refractory to known antibiotic agents, may be realized in the near future. Development of novel antimicrobial compounds is a continuing urgent public health need.

SUMMARY OF THE INVENTION

The invention features an antimicrobial composition comprising a substance P (SP) peptide or peptide mimetic thereof. The amino acid sequence of the peptide contains at least residues 1-8 of Arg-Pro-Lys-Pro-Gln-Gln-Phe-Phe-Gly-Leu-Met (SEQ ID No:1), or the amino acid sequence of the peptide contains at least residues 1-8 of Arg-D-Pro-Lys-Pro-Gln-Gln-D-Trp-Phe-D-Trp-Leu-Met (SEQ ID No: 2). A SP peptide is a peptide with antimicrobial activity, which contains an amino acid sequence that is at least 50% identical to the amino acid sequence of SEQ ID NO:1.

The peptide contains levorotatory (L) and/or dextrorotatory (D) forms of an amino acid. For example, the peptide has at least one D amino acid. The antimicrobial composition further contains one or more additional antimicrobial agents such as tetracycline, penicillin, doxycycline, ampicillin, or CIPRO™.

Antimicrobial peptides contain the amino acid sequence $Xaa_1$-Pro-$Xaa_2$-Pro-$Xaa_3$-$Xaa_4$-$Xaa_5$-$Xaa_6$ (SEQ ID NO:12). Referring to SEQ ID NO:12, $Xaa_1$ and $Xaa_2$ are positively charged amino acids, $Xaa_3$ and $Xaa_4$ are any amino acids other than Pro, and $Xaa_5$ and $Xaa_6$ are hydrophobic amino acids. $Xaa_5$ and $Xaa_6$ are preferably aromatic amino acids. For example, $Xaa_5$ and $Xaa_6$ are Phe or Trp. Preferably, the composition does not contain Saporin (U.S. Pat. No. 6,063,758), neither in a free form, nor conjugated to to the antimicrobial peptide.

The amino terminal portion of a SP peptide associates with a membrane component of a microbe. Preferably, the SP peptide associates with a microbial membrane component but does not associate with an SP receptor, e.g., a tachykinin receptor. Accordingly, the peptide contains amino acids 1-5, 1-6, 1-7, 1-8, 1-9, or 1-10 of SEQ ID NO:1 or 2, and lacks 1, 2, 3, 4, or 5 amino acids from the carboxy-terminal end of SEQ ID NO:1 or 2. The amino acid sequence of the peptide contains residues 1-10 of SEQ ID Nos: 1 or 2. For example, the amino acid sequence of the peptide comprises Arg-Pro-Lys-Pro-Gln-Gln-Phe-Phe-Gly-Leu-Xaa (SEQ ID NO:13), wherein Xaa is not a methionine residue.

The antimicrobial composition inhibits growth of a bacteria (e.g., cutaneous, mucosal, or enteric bacteria), fungus, or virus. For example with respect to bacteria, the peptide inhibits growth of a cell selected from the genera consisting of *Staphylococcus, Streptococcus, Bacillus, Clostridium, Escherichia, Shigella, Campylobacter, Hemophilus, Proteus, Yersinia, Klebsiella, Pseudomonas,* and *Serratia*. For example with respect to fungi, the peptide inhibits growth of a cell selected from the genera consisting of *Aspergillus, Candida, Cryptococcus, Epidermophyton, Histoplasma, Microsporum,* and *Trichophyton*.

The invention also includes a method for inhibiting growth or survival of a microorganism, by directly contacting the microorganism (e.g., a membrane component of the microbe) with a SP peptide or a peptide mimetic thereof. A peptide mimetic is an SP analog in which one or more peptide bonds have been replaced with an alternative type of covalent bond, and which is not susceptible to cleavage by peptidases elaborated by the subject or by the target microorganism. The peptide contains at least 8 consecutive residues, e.g., residues 1-8, of the amino acid sequence of SEQ ID Nos: 1 or 2. For example, the peptide contains at least positions 1-10 of the amino acid sequence of SEQ ID Nos: 1 or 2.

The invention also provides a method of inhibiting a microbial infection by carrying out the following steps: identifying a mammal suffering from or at risk of developing a microbial infection and administering to the mammal a SP peptide or peptide mimetic thereof. The peptide or peptide mimetic is administered topically. In an alternative embodiment, the invention provides a method of inhibiting a microbial infection, by introducing directly into an articulating joint of an animal a SP peptide or peptide mimetic thereof. The method is also carried out by introducing the SP peptide or mimetic directly into an abscess.

Also within the invention is a kit containing at least one unit dose of an antimicrobial SP peptide or mimetic packaged together with a label, instructions for use, or means of administering the compound "Antimicrobial" activity of an agent or composition shall mean ability to inhibit growth of one or more microorganism. For example, the antimicrobial compositions described herein inhibit the growth of or kill bacterial, algal, fungal, protozoan, and viral genera and species thereof.

It is well known to one of skill in the art of antibiotics development that an agent that causes inhibition of growth can also be lethal to the microorganism (bacteriocidal, for example in the case of a microorganism that is a bacterium). The SP peptide or mimetic is lethal, growth inhibitory, or both.

"Broad spectrum" antimicrobial activity means to ability to inhibit growth of organisms that are relatively unrelated. For example, ability of an agent to inhibit growth of both a Gram positive and a Gram negative bacterial species is considered a broad spectrum activity.

Various compositions and methods herein are useful for preventing and treating Gram positive and Gram negative bacterial infections in human and animal subjects. Gram positive bacterial species are exemplified by, but not limited to, genera including: *Staphylococcus*, such as *S. epidermis* and *S.* aureus; Micrococcus; Streptococcus, such as *S. pyogenes, S. equis, S. zooepidemicus, S. equisimilis, S. pneumoniae* and *S. agalactiae; Corynebacterium,* such as *C. pyogenes* and *C. pseudotuberculosis; Erysipelothrix* such as *E. rhusiopathiae; Listeria,* such as *L. monocytogenes; Bacillus,* such as *B. anthracis; Clostridium,* such as *C. perfringens*; and *Mycobacterium,* such as *M. tuberculosis* and *M. leprae.*

Gram negative bacterial species are exemplified by, but not limited to genera including: *Escherichia,* such as *E. coli* O157:H7; *Salmonella,* such as *S. typhi* and *S. gallinarum; Shigella,* such as *S. dysenteriae; Vibrio,* such as *V. cholerae; Yersinia,* such as *Y. pestis* and *Y. enterocolitica; Proteus,* such as *P. mirabilis; Bordetella,* such as *B. bronchiseptica; Pseudomonas,* such as *P. aeruginosa; Klebsiella,* such as *K. pneumoniae; Pasteurella,* such as *P. multocida; Moraxella,* such as *M. bovis; Serratia,* such as *S. marcescens; Hemophilus,* such as *H. influenza;* and *Campylobacter* species. Further examples of bacterial pathogenic species that are inhibited according to the invention are obtained by reference to standard taxonomic and descriptive works such as *Bergey's Manual of Determinative Bacteriology, 9th* Ed., 1994, Williams and Wilkins, Baltimore, Md.

Prevention and treatment of fungal infections are embodied by various compositions and methods provided herein. Suitable fungal genera are exempflied, but not limited to: *Candida,* such as *C. albicans; Cryptococcus,* such as *C. neoformans; Malassezia (Pityrosporum); Histoplasma,* such as *H. capsulatum; Coccidioides,* such as *C. immitis; Hyphomyces,* such as *H. destruens; Blastomyces,* such as *B. dermatiditis; Aspergillus,* such as *A. fumigatus; Penicillium,* such as *P. marneffei;* and *Pneumocystis,* such as *P. carinii.* Subcutaneous fungi, such as species of *Rhinosporidium* and *Sporothrix,* and dermatophytes, such as *Microsporum* and *Trichophyton* species, are amenable to prevention and treatment by embodiments of the invention herein.

Prevention and treatment of viral infections that are topically manifested are embodied by various compositions and methods provided herein. Suitable viral infections include but are not limited to: viral warts (papilloma virus), Herpes simplex type I and type II, varicella zoster (chicken pox), Molluscum contagiosum (a pox virus), rubeola (measles), and rubella (German measles).

A subject to be treated is an animal, preferably a warmblooded animal, including any bird or mammal species. Methods and compositions embodied herein are envisioned for human and veterinary use. Veterinary use includes application to cows, horses, sheep, goats, pigs, dogs, cats, rabbits, and all rodents. The methods of the invention are also useful to agricultural workers and pet owners to combat infections contracted by exposure to livestock or pet animals.

A subject is diagnosed as having a microbial infection by inspection of a bodily tissue, e.g., epidermal and mucosal tissue, including such tissue present in surfaces of oral, buccal, anal, and vaginal cavities and glans penis. Diagnosis of infection is made according to criteria known to one of skill in the medical arts, including but not limited to, areas of inflammation or unusual patches with respect to color, dryness, exfoliation, exudation, prurulence, streaks, or damage to integrity of surface. Conditions exemplary of those treated by the compositions and methods herein, such as abscess, meningitis, cutaneous anthrax, septic arthritis, emphysema, impetigo, cellulitis, pneumonia, sinus infection and tubercular disease are accompanied by elevated temperature. Diagnosis can be confirmed using standard ELISA-based kits, and by culture, and by traditional stains and microscopic examination of direct samples, or of organisms cultured from an inoculum from the subject.

Other features and advantages of the invention will be apparent from the following description of embodiments thereof, and from the claims.

DETAILED DESCRIPTION

Figure 1:
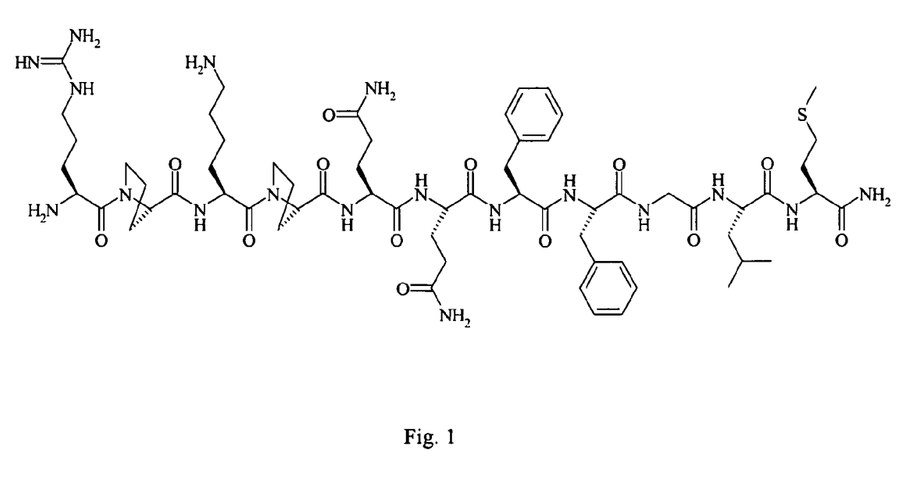
FIG. 1 is a diagram of the chemical structure of SP.

Naturally-occurring SP, a member of the tachykinin family, is an undecapeptide (SEQ ID NO:1, FIG. 1). SP plays a key role in pain signal transmission. As it is widely distributed not only in the central and peripheral nervous systems, but in other tissues as well, it also mediates multiple homeostatic functions. Some classes of immune cells, such as T and B cells, endothelial cells, and macrophages, have the ability to express SP receptors; and some classes of immune cells such as macrophages, eosinophils, and endothelial cells, have the ability to produce SP.

The concentration of SP increases in inflamed tissues, consistent with a role in mammalian host defense system. Naturally-occurring SP is involved in direct stimulation of lymphocytes and regulation of tissue repair via enhancement of proliferation of fibroblasts and endothelial cells. In addition, immune cells can be induced by SP to produce cytokines that modulate hematopoiesis. SP is involved in activation of multiple endogenous defense systems.

Surprisingly, the data herein show that compositions such as SP peptides, SP-related molecules, SP fragments, and SP peptide derivative compositions having a particular consensus amino acid sequence, possess broad spectrum antimicrobial activities.

Determination of SP-Mediated Antimicrobial Activity

Inhibition of growth (bacteriostasis, for example in the case of a microorganism that is a bacterium) is determined by turbidometric analysis of a liquid culture. For example, such that a culture having a particular titer of cells per unit volume in the presence of one or more concentrations of the agent fails to increase in density as measured by light scattering in a spectrophotometer or calorimeter, in comparison to the culture in the absence of the agent or at a lower concentration of the agent. Inhibition of growth is also determined using solid medium containing a concentration of the agent, such that a reduced ability to form a number of visible colonies (reduced titer of bacterial cells) is observed in the presence of that concentration of agent, in comparison to the absence of the agent or a lower concentration. The assays are standardized by using a predictable predetermined number of cells, and the lowest observed concentration of the agent that inhibits growth is defined as the minimum inhibitory concentration (MIC). With this parameter, an agent having a lower MIC than another has a greater antimicrobial activity for the organism used in the assay.

Anti-fungal activity is similarly assayed, using log phase vegetative fungal cells. Vegetative cells of a model non-pathogenic species such as *Saccharomyces cerevisiae,* a *Kluyveromyces* or a *Pichia* species, or a pathogenic species such as *Candida albicans* are grown in a nutrient broth such as a standard yeast medium, to log phase, and then assayed by liquid or solid medium methods, as described above for bacteria.

Methods of assay for antiviral activity are also known in the art. A first method is direct measurement of lethality for virions, such as mixing various concentrations of the antiviral agent, e.g., for a fixed time, or as a function of time, with a known number of "plaque forming units" (PFU) of the virus strain. The treated virus PFUs are then diluted and mixed with an appropriate number of sensitive cells, and the number of plaques obtained in comparison to the same number of PFUs that have been identically treated, in the absence of the antimicrobial compound. This assay detects activity that directly disrupts virion structure or initial function of interaction with a sensitive host cell.

A second method detects inhibition by the agent of ability of the virus to successfully replicate in a sensitive cell. In this method, a sample from each of a range of concentrations of the antiviral agent is added to infected cells at a particular time following the infection, e.g., simultaneous to infection, or within 10 min or one hour of infection. Progeny viruses are collected at the end of the replication cycle, e.g., at 20 h after infection and incubation of the infected cells. The reduction yield of progeny viruses from infected cells in the presence of the agent, and as a function of concentration of the agent, compared to the yield in the absence of the agent, indicates that the agent, e.g., a SP peptide, possesses antiviral activity.

SP Peptides

SP peptides contain an amino acid sequence related to that of positions 1-8 of the amino terminal amino acids in the sequence of SP or SP antagonist (as shown in SEQ ID No: 1 or 2). The peptide of SEQ ID NO:2 is referred to as an SP antagonist because it interferes with SP receptor-mediated SP activity. The antimicrobial activity of an SP peptide is unrelated to SP receptor binding. SP receptor binding involves the carboxy-terminal end of SP. The carboxy-terminal 1, 2, or 3 amino acids of SP are not required for antimicrobial activity.

SP peptides are at least 50% identical to the sequences of SEQ ID NO:1 or 2. Further, they are at least 75% identical, 85%, 95%, and 99% identical to the sequences of SEQ ID NO:1 or 2. Nucleotide and amino acid comparisons described herein are carried out using the Lasergene software package (DNASTAR, Inc., Madison, Wis.). The MegAlign module used is the Clustal V method (Higgins et al., 1989, CABIOS 5(2):151-153). The parameter used is gap penalty 10, gap length penalty 10.

The one letter and three letter codes for the 20 naturally occurring amino acids are well known to one of skill in the art, and are indicated herein as appropriate. Amino acids which are positively charged are lysine (lys, K) and arginine (arg, R). Aromatic amino acids are tyrosine (tyr, Y), phenylalanine (phe, F) and tryptophan (trp, W). The aromatic amino acids are classified further as hydrophobic amino acids, a group which further includes valine (val, V), leucine (leu, L), and isoleucine (ile, I). A conservative substitution of one amino acid for another is a replacement by an amino acid having a similar chemical functional side group, e.g., replacement of a positively charged amino acid by another positively charged amino acid, or replacement of a hydrophobic amino acid by another hydrophobic amino acid.

The antimicrobial activity of the SP peptides and peptide mimetics thereof are associated with the residues located at the amino terminus. The amino-terminal four amino acids of SP peptides are alternately basic residues, i.e., the positively charged amino acids lysine (lys, K) and arginine (arg, R), and proline residues. Reference to Table 1 shows that a consensus amino acid sequence among the SP peptides in these first four positions is an alternation of two basic amino acids and two proline residues. The alternation of basic positively charged residues and proline residues confers a particular structure to the SP peptide.

Peptide modification techniques are used in the manufacture of drug analogs of biological compounds and are known to one of ordinary skill in the art. Synthetic peptides having an antimicrobial activity that is at least 50% of that of SP are produced by either of two general approaches. In a first approach, the peptides are produced by the well-known Merrifield solid-phase chemical synthesis method wherein amino acids are sequentially added to a growing chain. See, Merrifield (1963) J. Am. Chem. Soc. 85:2149-2156. Systems for manually synthesizing peptides on polyethylene pegs are available from Cambridge Research Biochemicals, Cambridge, Mass. Automatic peptide synthesis equipment is available from several commercial suppliers, including Applied Biosystems, Inc., Foster City, Calif.; Beckman Instruments, Inc., Waldwick, N.J., and Biosearch, Inc., San Raphael, Calif. Using such automatic synthesizers according to manufacturer's instructions, peptides are produced in gram quantities for use in the present invention. This method is preferred as yielding an SP peptide in a substantially purified condition, free of contaminating cell components, and substantially free of contaminating chemicals used in the synthetic procedure.

A polypeptide is substantially pure when it constitutes at least about 60%, by weight, of the protein in the preparation. Preferably, the peptide in the preparation is at least about 75%, more preferably at least about 90%, and most preferably at least about 99%, by weight, of SP peptide or mimetic. Purity is measured by any appropriate method, e.g., column chromatography, polyacrylamide gel electrophoresis, or HPLC analysis. Accordingly, substantially pure peptides include peptides purified from natural sources, recombinant peptides derived from a eucaryote but produced in *E. coli* or another procaryote, or in a eucaryote other than that from which the peptide was originally derived as well as chemically-synthesized peptides.

In a second approach, the synthetic SP peptides of the present invention are prepared by recombinant techniques involving the expression in cultured cells of recombinant DNA molecules encoding a gene for a desired portion of a natural or analog SP molecule. The gene encoding the peptide is natural or synthetic. Polynucleotides are synthesized by well known techniques based on the desired amino acid sequence. For example, short single-stranded DNA fragments are prepared by the phosphoramidite method described by Beaucage et al. (1981) Tetra. Lett. 22:1859-1862. A double-stranded fragment is obtained either by synthesizing the complementary strand using DNA polymerase under appropriate conditions or by adding the complementary strand using DNA polymerase with an appropriate primer sequence. The natural or synthetic DNA fragments coding for the desired SP peptide is incorporated into a suitable DNA construct capable of introduction to and expression in an in vitro cell culture. A particular technique for the recombinant DNA production of SP is described in Yokota et al. (1989) J. Biol. Chem. 264:17649, the disclosure of which is incorporated herein by reference. According to this method, the peptide must be further purified away from contaminating cellular materials. A peptide is considered purified if it is at least about 90% free of material having a different chemical composition, e.g., at least about 95% free, and at least about 98-99% free of contaminating material, by weight.

The methods and the SP compositions in certain embodiments of the present invention employ synthetic SP peptide derivative compounds, which can comprise amino acid analogs such as D-amino acids, or which can be non-peptide compositions or peptide mimetics as described herein. The SP peptide derivative compounds and peptide mimetics have functional antimicrobial activity comparable to that of a known SP peptide. The antimicrobial activity is for example, from about one-half of activity of SP peptide, to about two-fold, about four-fold, or about ten-fold greater than that of SP Peptide.

The derivative compounds have a shape, size, flexibility, and electronic configuration such that the antimicrobial activity of the molecule is similar to a natural antimicrobial peptide. Such non-peptide molecules will typically be small molecules having a molecular weight in the range from about 100 to about 1000 daltons. The use of such small molecules is frequently advantageous both in preparation of pharmacological compositions, and in pharmacological properties such as bioavailability, permeability into the microbial target, rate of metabolism by the subject and the target microorganism, and stability.

The invention includes analogs in which one or more peptide bonds have been replaced with an alternative type of covalent bond (a "peptide mimetic") which is not susceptible to cleavage by peptidases elaborated by the subject or by the target microorganism. Where proteolytic degradation of a peptide composition is encountered following administration to the subject, replacement of a particularly sensitive peptide bond with a noncleavable peptide mimetic renders the resulting peptide derivative compound more stable and thus more useful as a therapeutic. Such mimetics, and methods of incorporating them into peptides, are well known in the art.

Similarly, the replacement of an L-amino acid residue by a D-amino acid residue is a standard method for rendering the compound less sensitive to enzymatic destruction. Other amino acid analogs are known in the art, such as norleucine, norvaline, homocysteine, homoserine, ethionine, and the like. Also useful is derivatizing the compound with an amino-terminal blocking group such as a t-butyloxycarbonyl, acetyl, methyl, succinyl, methoxysuccinyl, suberyl, adipyl, azelayl, dansyl, benzyloxycarbonyl, fluorenylmethoxycarbonyl, methoxyaselayl, methoxyadipyl, methoxysuberyl, and a 2,3-dinitrophenyl group. Blocking the charged amino- and carboxy-termini of the peptide derived compound would have the additional benefit of enhancing solubility of the compound in the hydrophobic environment of the cell membrane of the target microorganism.

The design of such peptide mimetic SP compounds is performed using techniques known in the art of drug design. Such techniques include, but are not limited to, self-consistent field (SCF) analysis, configuration interaction (CI) analysis, and normal mode dynamics computer analysis, all of which are well described in the scientific literature. See, e.g., Rein et al., Computer-Assisted Modeling of Receptor-Ligand Interactions, Alan Liss, NY (1989). Preparation of the identified compounds will depend on the desired characteristics of the compounds and will involve standard chemical synthetic techniques. See, Cary et al. Advanced Organic Chemistry, part B, Plenum Press, NY (1983).

Antimicrobial Formulations and Therapeutic Administration Thereof

The SP peptides, peptide analogs, and peptide mimetics are incorporated in a physiologically acceptable carrier or salt, suitable for topical application to the affected area, or for direct injection into the affected areas such as a soft tissue abscess or an infected joint, or for diffusion from a surgically implanted device. Topical applications include lavage of body cavities or lumens, e.g., pre- or post-surgical peritoneal lavage or pulmonary lavage. Topical applications include use of gels, creams, lotions, suppositories, and use of devices and dressings such as dissolving patches and bandages impregnated prior to use with the antimicrobial peptide. Additional routes of delivery include oral, and injection or infusion that is intramuscular, intravenous, subcutaneous, intraperitoneal, intraspinal, and epidural. Meningitis for example is treated by administration of an SP peptide by several routes, including direct intraspinal injection.

The compositions contain from about 0.1 nM to about 10 mM peptide, usually containing from about 0.01 µM to about 1 mM compound, and more usually containing from about 0.1 µM to about 100 µM of SP peptide or peptide derived compound. The nature of the carrier depends on the intended area of application. For application to the skin, a cream lotion, or ointment base is usually preferred, with suitable bases including lanolin, SILVADENE™, particularly for the treatment of burns; AOUAPHOR™ (Duke Laboratories, South Norwalk, Conn.), and the like. The peptides or derivative compounds are incorporated into or onto natural and synthetic bandages and other wound dressings to provide for continuous exposure of a wound to the peptide. Aerosol applicators and inhaler devices are used, for delivery to sinuses and deeper portions of the respiratory system. Peptides and derivative compounds are also incorporated in or coated on implantable devices, such as heart pacemakers, intralumenal stents, and the like where the antimicrobial activity would be of benefit. Coating is achieved by non-specific adsorption or covalent attachment. Optionally, an anti-pruritic agent such as an opioid is added to a antimicrobial composition to relieve pain at an infected site. Additional antimicrobial agents can be combined with the SP peptides, including but not limited to one or more of beta-lactam antibiotics such as penicillin, macrolides such as erythromycin, aminoglycosides such as lincomycin, tetracyclines such as doxycycline, semi-synthetic antibiotics such as Ceclor, and bacterially-derived peptide antibiotics such as gramicidin and tyrocidin.

The contents of all cited patents and papers are hereby incorporated by reference herein.

Example 1

Structure of SP and Derivatives Thereof

Peptides were synthesized by respective Boc- or Fmoc-chemistry in solid phase by methods known in the art, e.g., Misicka, et al., Biochemical & Biophysical Research Communications 1991:180(3):1290-7. Crude peptides were purified by gel filtration on Sephadex LH-20 (in methanol), followed by preparative HPLC. All peptides were confirmed to have correct amino acid analyses and molecular weights by FAB-MS. For microbiological study, peptides in acetate form were used. The sequences of the peptides are: SP, Arg-Pro-Lys-Pro-Gln-Gln-Phe-Phe-Gly-Leu-MetNH2 (FIG. 1, SEQ ID NO:1); SP antagonist, Arg-D-Pro-Lys-Pro-Gln-Gln-D-Trp-Phe-D-Trp-Leu-MetNH2 (SEQ ID NO:2); bradykinin, Arg-Pro-Pro-Gly-Phe-Ser-Pro-Phe-Arg (SEQ ID NO:3); neurotensin, Glu-Leu-Tyr-Glu-Asn-Lys-Pro-Arg-Arg-Pro-Tyr-Ile-Leu (SEQ ID NO:4) or Xaa-Leu-Tyr-Glu-Asn-Lys-Pro-Arg-Arg-Pro-Tyr-Ile-Leu (SEQ ID NO:14; where Xaa is Pyr or Tyr); and indolicidin, Ile-Leu-Pro-Trp-Lys-Trp-Pro-Trp-Trp-Pro-Trp-Arg-Arg-NH2 (SEQ ID NO: 5).

SP is expressed in a variety of different animals. Analysis of the sequences of these homologues, in comparison to that of humans (SEQ ID NO:1) yields insight into design of SP peptides embodied herein. The sequence of SP native to the following organisms has been reported:

TABLE 1

| | | |
|---|---|---|
| SEQ ID NO:6 | spotted dogfish | Lys-Pro-Arg-Pro-Gly-Gln-Phe-Phe-Gly-Leu-Met |
| SEQ ID NO:7 | guinea pig, horse, cow | Arg-Pro-Lys-Pro-Gln-Gln-Phe-Phe-Gly-Leu-Met |
| SEQ ID NO:8 | alligator, chicken | Arg-Pro-Arg-Pro-Gln-Gln-Phe-Phe-Gly-Leu-Met |
| SEQ ID NO:9 | Atlantic cod | Lys-Pro-Arg-Pro-Gln-Gln-Phe-Ile-Gly-Leu-Met |
| SEQ ID NO:10 | rainbow trout | Lys-Pro-Arg-Pro-His-Gln-Phe-Phe-Gly-Leu-Met |
| SEQ ID NO:11 | sea lamprey | Ala-Lys-His-Asp-Lys-Phe-Tyr-Gly-Leu-Met |
| SEQ ID NO:1 | human | Arg-Pro-Lys-Pro-Gln-Gln-Phe-Phe-Gly-Leu-Met |

These data indicate a fully conserved consensus from pre-vertebrate chordate animals to humans, located in the three C-terminal residues. These three residues confer on the SP the ability to interact with a specific SP receptor on immune cells. Further, a consensus in the 8 N-terminal positions is found to be: $Xaa_1$-Pro-$Xaa_2$-Pro-$Xaa_3$-$Xaa_4$-$Xaa_5$-$Xaa_6$ (SEQ ID NO:12) where $Xaa_1$ and $Xaa_2$ are positively charged amino acids, $Xaa_3$ and $Xaa_4$ are Gln or Gly, and $Xaa_5$ and $Xaa_6$ are aromatic amino acids, particularly Phe. This 8-residue fragment of SP has antimicrobial activity but cannot bind to an SP receptor on a cell of a subject, since the fragment lacks the portion of the peptide that confers affinity to that receptor.

Without being bound by any particular mechanism, antimicrobial activity of SP peptides requires the above 8-residue consensus sequence. The aromatic residues confer solubility on the peptide for the hydrophobic lipids of the membrane of target microbe cells, and also confer the ability for self-aggregation and multimerization of the SP peptide. The alternating positive residues and prolines at positions 1-4 of the 8-mer peptide confer a particular three dimensional configuration, for example, a helical configuration, to the monomer, so that the monomer assoicates with a lipid moiety of a cell membrane. SP peptides interact with one another and with a component of a microbial membrane to form a supramolecular structure, e.g., a pore.

Peptides having the above consensus offer advantages for use as a novel antimicrobial agent. As SP is an endogenous peptide, found in humans and other chordate and vertebrate animals, it is not antigenic. Therefore continued administration of this agent over time does not provoke an immune response. Further, deletion or substitution one or more of the three carboxy-terminal residues (Gly-Leu-Met) associated with affinity of the SP peptides to a specific SP receptor on cells of the immune system assures that possible undesired side affects of systemic SP administration (e.g., SP-receptor mediated activities such as pain, inflammation, and swelling) are reduced or eliminated. In addition, the antimicrobial activity of SP peptides has a broad antimicrobial spectrum as shown herein, including Gram positive and Gram negative bacteria, and fungi. These data indicate that traditional targets for antimicrobial agents, such as the prokaryotic ribosome or the murein cross-bridges of a bacterial cell wall are not involved as macromolecular targets. Therefore, the compounds described herein cannot be evaded by enzymes associated with multiple drug resistance factors. Topical administration of an SP peptide to an epithelium of a subject offers the advantage that the peptide remains external and does not become systemic.

Example 2

Antimicrobial Activity of SP and Derivatives Using Bacterial Test Species

Antimicrobial activity, specifically antibacterial activity, was assayed using cells of each of *Staphylococcus aureus* NCTC 4163, *Escherichia coli* NCTC 8196, *Pseudomonas aeruginosa* NCTC 6749, *Proteus vulgaris* NCTC 4635, and *Enterococcus faecalis* ATCC 19212. To determine the minimum inhibitory concentration (MIC), the microdilution broth method, well-known to one of ordinary skill in the art of microbiology, was used. Cells of each bacterial strain were collected in the logarithmic phase of growth, and resuspended in nutrient broth. The concentration of colony-forming units (CFU) per milliliter was quantified by measuring absorption of light at 600 nm ($A_{600}$).

Peptide samples were dissolved in nutrient broth (pH 7.0) and diluted serially. The sample solution (100 µl) was mixed with the diluted bacterial suspension (100 µl). Mixtures containing 105 bacterial CFU, and from 1% to 0.003% of test peptides, were incubated for 24 h at 37° C. Antimicrobial activities were expressed as the minimal inhibitory concentration (MIC), which is defined as the concentration at which 100% inhibition of growth of this number of cells was observed (Table 2). The indolicidin antibacterial property with cells of *S. aureus* was used as a positive control reference.

TABLE 2

Antimicrobial activities of SP peptides, neurotensin and bradykinin

| | Minimal Inhibitory Concentration MIC (%) | | | | | |
|---|---|---|---|---|---|---|
| | S. aureus | E. coli | E. faecalis | P. vulgaris | P. aeruginosa | C. albicans |
| SEQ ID NO: 1 | 0.007 | 0.06 | 0.13 | 0.13 | 0.13 | 0.25 |
| SEQ ID NO: 2 | 0.13 | 0.13 | 0.13 | 0.13 | 0.13 | 0.03 |
| Neurotensin | 0.25 | 1.0 | 1.0 | 0.5 | 1.0 | >1 |
| Bradykinin | 0.5 | 0.5 | >1 | 0.5 | 1.0 | 0.25 |
| Indolicidin | 0.003 | 0.007 | n.t* | n.t. | n.t. | 0.015 |

*n.t.—not tested

Naturally-occurring SP binds to a specific SP receptor on certain cells and plays an active role in the host defense system. This peptide, and other regulatory peptides such as neurotensin and bradykinin, exhibit coordinated actions in protecting mammals from microbial infection. Previously, all activities of substance P have been related to its effects on endogenous mechanisms activated by NK receptors, such as antibody stimulation (Maszczynska, et al., Analgesia 2000; 3:259-68; Hartung, et al., Journal of Immunology 1986; 136 (10):3856-63; Jeon, et al., Immunopharmacology 1999; 41 (3):219-26; Pascual and Bost, Immunology 1990; 71(1)52-5; Linnik and Moskowitz, Peptides 1989; 10(5):957-62; Payan, Annual Review of Medicine 1989; 40:341-52); histamine release; (Shibata, et al., Biochimica et Biophysica Acta 1985; 846(1): 1-7); induction of NO synthesis (Hartung, et al., Journal of Immunology 1986; 41(3):219-26); vasodilation, and so on (Joos and Pauwels, Trends in Pharmacological Sciences 2000; 21(4): 131-3).

In addition to SP, other peptides (e.g., neurotensin, bradykinin), which are expressed also at sites and injured tissues that form the frontiers of the host defense system, were tested. Surprisingly, a variety of pathogenic microorganisms were found to be inhibited by SP peptides with the amino acid sequence of SEQ ID NO:1 and 2. Bradykinin and neurotensin had significantly lower antibacterial potency than either SP or SP antagonist against nearly all microorganisms tested.

Data obtained using cells of *S. aureus* demonstrate that SP and SP derivatives thereof have substantial antimicrobial activity. The level of activity was comparable to that of indolicidin. The antimicrobial property of SP was found to be very strong (Table 2), i.e., equally potent to indolicidin for cells of the Gram positive bacterial species *S. aureus*. Further, SP antagonist activity is comparable to that of indolicidin for cells of the fungal pathogen *C. albicans*.

The antimicrobial potencies of SP antagonist on the other bacteria tested were weaker than SP (MIC was 10- to 20-fold higher), but still significant. Observed differences in activity correlate with endogenous recognition of pathogenic (*S. aureus*) and symbiotic bacteria (*E. coli*). *S. aureus* is widely and normally found on skin and so is "symbiotic" species, whereas infection by some strains of *E. coli*, such as the enterotoxic strain O157:H7, can be fatal.

Example 3

Antifungal Activity of SP and SP Antagonist

Antifungal activity was assayed using *Candida albicans* NCTC 10231 as a target fungus. *Candida* cells in the logarithmic phase of growth were suspended in dextrose broth medium at a density of $10^5$ CFU/ml. A mixture of the sample solution (100 µl) and the fungal suspension (100 µl) was incubated for 24 h at 37° C. Antifungal activity was assessed using turbidity measurement as described above (Table 2).

SP was found to have antifungal properties against *C. albicans*. Further, the SP antagonist was found to have approximately 10 times higher potency against *C. albicans* than either SP or bradykinin.

Example 4

SP Antagonist does not Affect the Antimicrobial Activity of SP

Using mixing experiments, the antimicrobial effect of SP was found not to be blocked by the presence of a SP antagonist. This finding confirms the data in Table 2, and indicates that the antimicrobial effect in vivo is not mediated by the SP receptor, but is rather a direct effect on the microorganism. Data herein indicate that substance P possesses previously unreported, direct antimicrobial potency.

Other embodiments are within the following claims.

What is claimed is:

1. A method for inhibiting growth or survival of a bacterial or fungal microorganism, comprising directly contacting the bacterial or fungal microorganism with a purified substance P peptide, wherein the purified substance P peptide comprises the amino acid sequence of SEQ ID NO:1.

2. The method of 1, wherein the bacteria is selected from the group of cutaneous, mucosal, or enteric bacteria.

3. The method of claim 1, wherein said bacterial microorganism is *Staphylococcus aureus, Escherichia coli, Pseudomonas aeruginosa, Proteus vulgaris,* or *Enterococcus faecalis*.

4. The method of claim 1, wherein said fungal microorganism is *Candida albicans*.

* * * * *

SEQUENCE LISTING

<160> NUMBER OF SEQ ID NOS: 14

<210> SEQ ID NO 1
<211> LENGTH: 11
<212> TYPE: PRT
<213> ORGANISM: Homo sapiens

<400> SEQUENCE: 1

Arg Pro Lys Pro Gln Gln Phe Phe Gly Leu Met
 1               5                  10

<210> SEQ ID NO 2
<211> LENGTH: 11
<212> TYPE: PRT
<213> ORGANISM: Homo sapiens
<220> FEATURE:
<221> NAME/KEY: VARIANT
<222> LOCATION: (2)
<223> OTHER INFORMATION: Wherein Pro is D-proline
<220> FEATURE:
<221> NAME/KEY: VARIANT
<222> LOCATION: (7)
<223> OTHER INFORMATION: Wherein Trp is D-tryptophan
<220> FEATURE:
<221> NAME/KEY: VARIANT
<222> LOCATION: (9)
<223> OTHER INFORMATION: Wherein Trp is D-tryptophan

```
<400> SEQUENCE: 2

Arg Pro Lys Pro Gln Gln Trp Phe Trp Leu Met
 1               5                  10

<210> SEQ ID NO 3
<211> LENGTH: 9
<212> TYPE: PRT
<213> ORGANISM: Homo sapiens

<400> SEQUENCE: 3

Arg Pro Pro Gly Phe Ser Pro Phe Arg
 1               5

<210> SEQ ID NO 4
<211> LENGTH: 13
<212> TYPE: PRT
<213> ORGANISM: Homo sapiens

<400> SEQUENCE: 4

Glu Leu Tyr Glu Asn Lys Pro Arg Arg Pro Tyr Ile Leu
 1               5                  10

<210> SEQ ID NO 5
<211> LENGTH: 13
<212> TYPE: PRT
<213> ORGANISM: Homo sapiens

<400> SEQUENCE: 5

Ile Leu Pro Trp Lys Trp Pro Trp Trp Pro Trp Arg Arg
 1               5                  10

<210> SEQ ID NO 6
<211> LENGTH: 11
<212> TYPE: PRT
<213> ORGANISM: Scyliorhinus canicula

<400> SEQUENCE: 6

Lys Pro Arg Pro Gly Gln Phe Phe Gly Leu Met
 1               5                  10

<210> SEQ ID NO 7
<211> LENGTH: 11
<212> TYPE: PRT
<213> ORGANISM: Cavia porcellus

<400> SEQUENCE: 7

Arg Pro Lys Pro Gln Gln Phe Phe Gly Leu Met
 1               5                  10

<210> SEQ ID NO 8
<211> LENGTH: 11
<212> TYPE: PRT
<213> ORGANISM: Gallus gallus

<400> SEQUENCE: 8

Arg Pro Arg Pro Gln Gln Phe Phe Gly Leu Met
 1               5                  10

<210> SEQ ID NO 9
<211> LENGTH: 11
<212> TYPE: PRT
<213> ORGANISM: Gadus morhua

<400> SEQUENCE: 9
```

```
Lys Pro Arg Pro Gln Gln Phe Ile Gly Leu Met
 1               5                   10

<210> SEQ ID NO 10
<211> LENGTH: 11
<212> TYPE: PRT
<213> ORGANISM: Oncorhynchus mykiss

<400> SEQUENCE: 10

Lys Pro Arg Pro His Gln Phe Phe Gly Leu Met
 1               5                   10

<210> SEQ ID NO 11
<211> LENGTH: 10
<212> TYPE: PRT
<213> ORGANISM: Petromyzon marinus

<400> SEQUENCE: 11

Ala Lys His Asp Lys Phe Tyr Gly Leu Met
 1               5                   10

<210> SEQ ID NO 12
<211> LENGTH: 8
<212> TYPE: PRT
<213> ORGANISM: Artificial Sequence
<220> FEATURE:
<221> NAME/KEY: VARIANT
<222> LOCATION: (1)
<223> OTHER INFORMATION: Wherein Xaa is His or Lys or Arg
<220> FEATURE:
<221> NAME/KEY: VARIANT
<222> LOCATION: (3)
<223> OTHER INFORMATION: Wherein Xaa is His or Lys or Arg
<220> FEATURE:
<221> NAME/KEY: VARIANT
<222> LOCATION: (5)
<223> OTHER INFORMATION: Wherein Xaa is not Pro
<220> FEATURE:
<221> NAME/KEY: VARIANT
<222> LOCATION: (6)
<223> OTHER INFORMATION: Wherein Xaa is not Pro
<220> FEATURE:
<221> NAME/KEY: VARIANT
<222> LOCATION: (7)
<223> OTHER INFORMATION: Wherein Xaa is Phe or Tyr or Trp
<221> NAME/KEY: VARIANT
<222> LOCATION: (8)
<223> OTHER INFORMATION: Wherein Xaa is Phe or Tyr or Trp
<220> FEATURE:
<223> OTHER INFORMATION: Description of Artificial Sequence:Consensus
      sequence

<400> SEQUENCE: 12

Xaa Pro Xaa Pro Xaa Xaa Xaa Xaa
 1               5

<210> SEQ ID NO 13
<211> LENGTH: 11
<212> TYPE: PRT
<213> ORGANISM: Artificial Sequence
<220> FEATURE:
<221> NAME/KEY: VARIANT
<222> LOCATION: (11)
<223> OTHER INFORMATION: Wherein Xaa is not Met
<220> FEATURE:
<223> OTHER INFORMATION: Description of Artificial Sequence:Consensus
      sequence

<400> SEQUENCE: 13

Arg Pro Lys Pro Gln Gln Phe Phe Gly Leu Xaa
 1               5                   10
```

```
<210> SEQ ID NO 14
<211> LENGTH: 13
<212> TYPE: PRT
<213> ORGANISM: Homo sapiens
<220> FEATURE:
<221> NAME/KEY: VARIANT
<222> LOCATION: (1)
<223> OTHER INFORMATION: Wherein Xaa is Pyr or Tyr

<400> SEQUENCE: 14

Xaa Leu Tyr Glu Asn Lys Pro Arg Arg Pro Tyr Ile Leu
 1               5                  10
```